United States Patent [19]

Palin et al.

[11] 4,225,783

[45] Sep. 30, 1980

[54] DETERMINATION OF MICROBIAL CELLS IN AQUEOUS SAMPLES

[75] Inventors: William J. Palin, Gurnee; Timothy C. Miller, Vernon Hills, both of Ill.

[73] Assignee: Abbott Laboratories, North Chicago, Ill.

[21] Appl. No.: 927,323

[22] Filed: Jul. 24, 1978

[51] Int. Cl.$^2$ .................... C12Q 1/29; G01N 21/00; G01N 33/48
[52] U.S. Cl. .................... 250/302; 356/39; 424/3; 424/7; 424/8; 424/12; 435/7; 435/29; 23/230 B
[58] Field of Search ............ 424/3, 7, 8, 12, 2; 250/302; 23/230 B; 356/39; 435/7, 29

[56] References Cited

U.S. PATENT DOCUMENTS

| | | | |
|---|---|---|---|
| 3,826,613 | 7/1974 | Parikh | 424/12 X |
| 3,853,987 | 12/1974 | Dreyer | 424/1 |
| 3,859,526 | 1/1975 | Hirschfeld | 250/302 |
| 3,957,741 | 5/1976 | Rembaum | 210/31 C X |
| 4,020,151 | 4/1977 | Bolz | 424/1.5 |
| 4,025,393 | 5/1977 | Hirschfeld | 195/103.5 M |
| 4,035,316 | 7/1977 | Yen | 260/2.5 B |
| 4,076,419 | 2/1978 | Kleker | 424/2 X |

FOREIGN PATENT DOCUMENTS

| | | | |
|---|---|---|---|
| 1475317 | 6/1977 | United Kingdom | 424/7 |
| 1475318 | 6/1977 | United Kingdom | 424/7 |

OTHER PUBLICATIONS

Bradford, J. of App. Phys. vol. 26, No. 7 Jul. 1955 pp. 864–869.
Molday, J. of Cell Biol. vol. 64, 1975 pp. 75–88.
Frobisher, Fund. of Microbiol, W. B. Saunders, Phila 8th Ed. 1970 pp. 45–48.
Klapper, Applied Microbiol, vol. 10, 1962 pp. 487–491.
Anderson, J. of Bacti, vol. 90, 1965 pp. 1764–1767.
Callis et al., Am. J. Hum. Genet. vol. 28, 1976 pp. 577–584.
Cytogenet. Cell Genet., vol. 19, 1977, pp. 94–107.

Primary Examiner—Anna P. Fagelson
Attorney, Agent, or Firm—John J. McDonnell

[57] ABSTRACT

The present invention encompasses a method for enumerating microbial cells in an aqueous test sample comprising: fluorescently labeling the microbial cells in test sample intermixing a known amount of monodispersed fluorescently labeled beads of about cell size into the test sample, and determining the ratio of bacterial cells to fluorescently labeled beads, the reagents for practicing this method. The methods and reagents of the present invention are particularly useful in counting bacterial cells in urine.

2 Claims, No Drawings

DETERMINATION OF MICROBIAL CELLS IN AQUEOUS SAMPLES

BRIEF DESCRIPTION OF THE INVENTION

The present invention encompasses a method for counting bacterial cells in an aqueous test sample comprising: fluorescent labeling of the bacterial cells, intermixing with the test sample a known amount of monodispersed fluorescently labeled beads of about cell size, and determining the ratio of bacterial cells to fluorescently labeled beads.

The present invention utilizes a reagent solution, made up of a sufficient concentration of fluorescent dye, which also contains a known amount of monodispersed fluorescently labeled beads of approximately the size of the cells. For example, if the final dilution of reagent and test sample contains $10^5$ cell/ml monodispersed fluorescently labeled beads and the stained cells and beads are determined under a fluorescent microscope to be equal number, the urine contains $10^5$ cells/ml.

DETAILED DESCRIPTION OF THE INVENTION

Monodispersed fluorescently labeled beads are well known in the art. U.S. Pat. No. 4,035,316, U.S. Pat. No. 3,853,987; *Journal of Cell Biology,* 64, 75 (1975), *Journal of Applied Physics,* 26 (7), 864 (1955); and U.S. Pat. No. 3,957,741.

Fluorescent dyes exemplified by Fluorescein, 4-6-diamidino-2-phenylindole, rhodamine, 9-aminoacridine-HCl, fluoresceinisothiocyanate, ε-dasyl-L-lysine dyes are bound to beads about 0.1–4 microns in diameter, about cell size, preferably about 2 microns. Fluoresbrite-fluorescent monodispersed carboxylated microspheres 1.83 micron diameter fluorescently labeled with 4-6-diamidino-2-phenylindole is a preferred monodispersed fluorescently labeled bead. Those skilled in the art will recognize a wide variety of dyes and material for produce fluorescing beads suitable for practicing the present invention.

Solutions of ethidium bromide, propidium iodide, phloxin, quinacrine hydrochloride, acridine orange and other cytophilicfluorochromes are representative suitable microbial cell labeling fluorescent dyes. Concentration range from 0.5–100 ng/ml, preferrably about 55 µg/ml in the reagent solution and about 5 µg/ml in test sample. Those skilled in the cell dying arts will recognize a wide variety of suitable dyes and concentration thereof to form an effective cell labeling amount of fluorescent dye.

A preferred reagent is a reagent solution in 2M Tris. HCl pH 9, 2-amino-2-hydroxymethyl-bis-propanediol-HCl containing 55.0 µg/ml of acridine orange and $1.0 \times 10^6$/ml of monodispersed fluorescent latex beads (1.83 micron diameters—Polyscience, Inc.).

In practice 100 µl of the above reagent is added to 1 ml of urine giving a concentration of acridine orange of 5 µg/ml and $1 \times 10^5$ beads/ml. A drop of the urine sample treated with reagent is then examined visually using a fluorescent microscope to compare the number of beads to cells. If the number of beads is less than the number of bacteria the bacterial cells must exceed $1 \times 10^5$ cells/ml and a clinical definition of a urinary tract infection is obtained.

Most urinary tract infections result from ascending infection by organisms introduced through the urethra. Acute infections are more common in females than in males because of the shorter urethra and the greater likelihood of its contamination in females. Infections are usually associated with bacterial counts of 100,000 ($10^5$) or more organisms per ml of urine (significant bacteriuria). This is because urine is an excellent culture medium for most organisms which infect the urinary tract, and growth occurs in the urine itself in vivo, resulting in high counts in established untreated infections. In contrast, contamination from the external genitalia, in the absence of infection, usually contributes less than 1,000 ($10^3$) organisms per ml in properly collected and transported specimens.

What is claimed is:

1. A method for enumerating bacterial cells in urine comprising adding to a urine sample an effective bacterial cell labeling amount of fluorescent dye and a known number per ml of urine of monodispersed fluorescently labeled beads of about cell size and determining the ratio of fluorescently labeled bacterial cells to fluorescently labeled beads.

2. A method according to claim 1 wherein about $10^5$ per ml of urine of monodispersed fluorescently labeled beads are added to the urine.

* * * * *